United States Patent [19]
Gunz et al.

[11] Patent Number: 5,444,232
[45] Date of Patent: Aug. 22, 1995

[54] ANTIGLARE DEVICE TO PROTECT EYES DURING WELDING AND IMMEDIATELY THEREAFTER FOR A TIME BASED ON THE INTENSITY AND DURATION OF THE WELDING LIGHT

[75] Inventors: Stefan Gunz, Wädenswil; Livio Ghisleni, Wilen; Manfred Castelberg, Wädenswil, all of Switzerland

[73] Assignee: Xelux AG, Switzerland

[21] Appl. No.: 223,754

[22] Filed: Apr. 6, 1994

[30] Foreign Application Priority Data

May 14, 1993 [CH] Switzerland .................. 1488/93

[51] Int. Cl.⁶ .................................................. G01J 1/20
[52] U.S. Cl. ............................ 250/201.1; 250/205; 2/8
[58] Field of Search ............... 250/201.1, 214 RC, 205; 359/63, 66, 68; 219/147; 2/8

[56] References Cited

U.S. PATENT DOCUMENTS

| | | | |
|---|---|---|---|
| 3,575,491 | 4/1971 | Heilmeier | 350/160 |
| 3,873,804 | 3/1975 | Gordon | 219/147 |
| 4,237,557 | 12/1980 | Gordon | 2/8 |
| 4,240,974 | 12/1980 | Hornell | 350/335 |
| 4,279,974 | 7/1981 | Belgorod | 350/331 R |
| 4,293,757 | 10/1981 | Niemi | 219/147 |
| 4,694,141 | 9/1987 | Hahn | 219/147 |
| 4,701,021 | 10/1987 | Le Pesant et al. | 350/267 |
| 5,248,880 | 9/1993 | Fergason | 250/205 |
| 5,252,817 | 10/1993 | Fergason et al. | 250/205 |
| 5,315,099 | 5/1994 | Gunz et al. | 250/201.1 |

FOREIGN PATENT DOCUMENTS

| | | |
|---|---|---|
| 0157744 | 10/1985 | European Pat. Off. |
| 2373808 | 7/1978 | France. |
| 2379127 | 8/1978 | France. |
| 2606416 | 9/1977 | Germany. |
| 2747614 | 10/1977 | Germany. |
| 1595842 | 8/1981 | United Kingdom. |

*Primary Examiner*—David C. Nelms
*Assistant Examiner*—Steven L. Nichols
*Attorney, Agent, or Firm*—Wigman, Cohen, Leitner & Myers

[57] ABSTRACT

An antiglare device, as used in the welding and cutting torch technology, comprising an electro-optical protective light filter and a controller. The electronics of the controller is designed in such a manner that in the case of a glare the protective light filter dims as rapidly as possible, but as soon as the source of glare light extinguishes the brightening time can be controlled as a function of the duration and intensity of the glare light.

15 Claims, 1 Drawing Sheet

ANTIGLARE DEVICE TO PROTECT EYES DURING WELDING AND IMMEDIATELY THEREAFTER FOR A TIME BASED ON THE INTENSITY AND DURATION OF THE WELDING LIGHT

CROSS-REFERENCE TO RELATED APPLICATION

This application relates generally to the subject matter contained in application 07/995,145 filed Dec. 22, 1992 in the name of the applicants herein, now U.S. Pat. No. 5,315,009.

BACKGROUND OF THE INVENTION

The present invention relates to an antiglare device, suitable for glasses, helmets and masks.

Antiglare devices are widely used in the welding and cutting torch technology, but are also used in the military and entertainment industries. As a rule, with these antiglare devices the radiation above 780 nm (infrared) and below 365 nm (ultraviolet) are filtered and only the radiation in the visible range is dimmed.

For example, in German patent DE 2,606,416, antiglare devices with a liquid crystal cell arranged between two polarizing sheets are described. This liquid crystal exhibits a frequency-dependent anisotropy of the dielectric constant, i.e., changes its homeotropic orientation as a function of the applied frequency of the electric alternating field. The switching times that can be realized in such a manner, i.e., the dimming time, respectively brightening time, are about 50 msec.

In U.S. Pat. No. 3,575,491, an electronic circuit is described for the purpose of operating liquid crystal cells in order to reduce the switching times to as far as 0.5 msec. This circuit functions with a voltage exceeding 125V.

In these known antiglare devices the switching time is device specific, i.e., depends on the respective construction, electronic circuit and the components that are used. The currently useful antiglare devices are characterized by unusually short switching times and low output.

However, it has been demonstrated that the short switching times are absolutely necessary for the darkening phase, but are not always desired for the brightening phase. In particular, when welding hot welding materials with long after-glow time, short brightening times result in intensive glares immediately after completion of the welding process.

On the other hand, short welding times can be necessary especially for spot or tack welding, as for example, to enable the work to be done rapidly with short cycles.

OBJECTS AND SUMMARY OF THE INVENTION

Based on the shortcomings of the prior art, an object of the present invention is to provide a device which can automatically detect what the brightening time should be, to reliably protect the user of the antiglare device, but not to hinder him in his work rhythm.

Another object of the present invention is to provide a device that detects the absolute light intensity, the respective amount of light and the welding duration, and interconnects these parameters in a meaningful manner with respect to logic and/or time by means of suitable electronics, thereby optimizing the brightening time to the given circumstances.

Still another object of the present invention is to provide a device whereby the change in the light intensity in the course of the welding process and the length of the welding interruption are detected and evaluated.

These objects are carried out by means of an antiglare device suitable for glasses, helmets and masks, as used in the welding and cutting torch technology, comprising a protective light filter, a photosensor detector electronics adapted to produce a dimming signal, evaluating electronics which control an electro-optical protective light filter, a controller to control the brightening time of the protective light filter, said controller detecting at least the intensity of the light impinging on the sensor; said controller being objectively connected to a timing generator to detect at least the duration of the dimming signal produced by the detector electronics; and said controller including means to interlink the acquired data with respect to logic and/or time.

Thus, the device according to the invention allows the brightness of the welding arc (caused by the varying intensity of flows, different materials, etc.) to be varied in order to control the brightening time and thus provides a universally useable antiglare device.

Moreover, the anitglare device according to the invention enables unimpeded work and simultaneously guarantees the necessary safety during use of these devices by professionals.

BRIEF DESCRIPTION OF THE DRAWINGS

The antiglare device according to the invention shall be explained in detail with reference to the drawings and the description which follows, wherein.

DETAILED DESCRIPTION OF THE PREFERRED EMBODIMENTS

Figure 1:
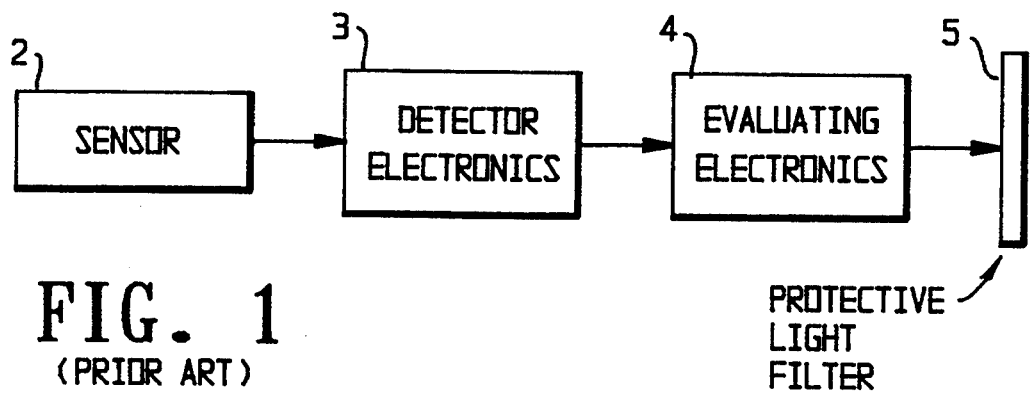
FIG. 1 is a block diagram of a conventional antiglare device.

The prior art antiglare device shown in FIG. 1 includes a sensor 2, which detects the amount of light produced in the user's range of vision and produces a corresponding signal. This signal is fed to detector electronics 3, which comprises in essence a threshold circuit. The on/off signal produced by this threshold circuit is fed to evaluating electronics 4, which prepares this on/off signal in such a manner that a protective light filter 5 can be switched as rapidly as possible.

Figure 2:
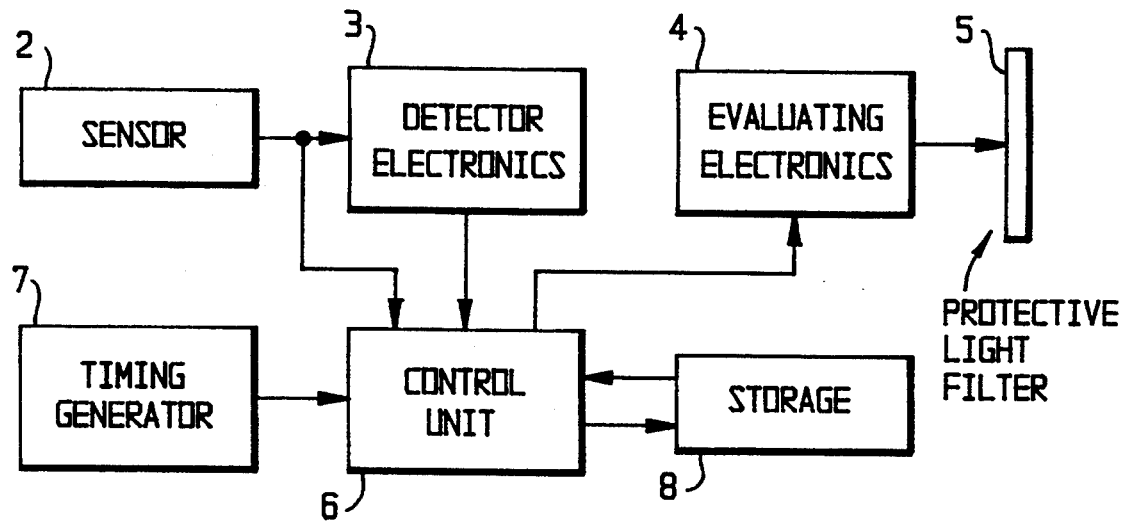
FIG. 2 is a block diagram of an antiglare device according to the invention.

In contrast, the antiglare device of the present invention as shown in the block diagram in FIG. 2 includes a control unit 6, connected to a timing generator 7 and a storage 8. Control unit 6 directly detects the signal, produced by the sensor 2, and further evaluates it. In particular, control unit 6 detects the intensity of the light impinging on the sensor 2 and generates a signal that corresponds to this amount of light and whose value is deposited in the storage 3, in order to suitably increase—within the specified limits—the brightening time of the protective light filter 5.

The signal produced by the detector electronics 3 is also fed to the control unit 6 and interlinked with respect to logic and/or time to the signal of the sensor 2 in a conventional manner well known to a person skilled in the art, in order to control the brightening time in a desired and/or mandatory manner.

In another embodiment, the detected and/or generated signals are used in order to control the dark/bright transition during the brightening time, i.e., produce a sudden, respectively slow, transition.

In particular, the detected duration of the welding process and/or the course of the signal generated by the sensor 2 can be detected at the start, during and at the close of the glare phase and serve(s) to generate a reset signal.

In a simplified embodiment the slope of the dark/bright transition is a direct function of the generated brightening time. It should also be understood that a manual stepped protection adjustment is provided for the antiglare devices, as used professionally by welders. According to the present invention, the protection step selected by the user and its manual fine adjustment can also be used to control the slope of the dark/bright transition.

Figure 3:
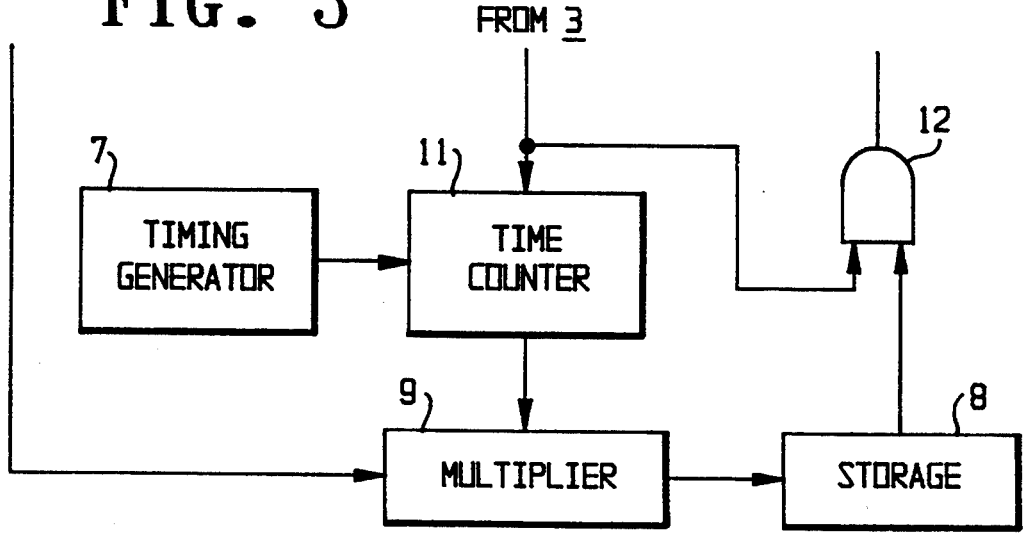
FIG. 3 is a block diagram of a suitable control unit used in conjunction with the device of the present invention.

FIG. 3 depicts in schematic form an embodiment for the time and/or logic operation of the first and second switching signals. In this embodiment the second switching signal produced by the detector circuit 3 is fed to a logical OR circuit 12 and thus allows the protective light filter 5 to darken immediately in the case of a glare situation. The on/off signal of the detector electronics 3 is also fed to a time counter 11 connected to the timing generator 7. This time counter in turn is connected to a multiplier circuit 9 and activates it during the glare phase. At the same time the multiplier circuit 9 is fed directly with the first switching signal generated by the sensor 2 and produces a corresponding signal value, which is deposited in the storage 8.

If the detector electronics 3 generates an off signal, the OR circuit 12 prevents the protective light filter 5 from brightening until a reset signal, which is delayed in accordance with the storage content, sets the counter 11 back to zero again and thus deactivates the multiplier circuit 9. The delay of the reset signal corresponds in the present example to the product of the time of the glare phase and the intensity of the glare light.

The electronic wiring of the control unit 6 lies within the normal capacities of a person skilled in the art and can be built both from individual components, integrated subassemblies or a suitable microprocessor. The use of other sensors 2 or storage units 8 to improve and optimize the antiglare device according to the invention is obvious to the expert.

Thus the antiglare device according to the invention can be used universally, i.e., allows during spot and tack welding a rapid and unimpeded working rhythm and ensures obscuration during the afterglow period which endangers the eyes during long-term welding.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. Antiglare device suitable for glasses, helmets and masks, as used in the welding and cutting torch technology, comprising a protective light filter, a photosensor detector electronics adapted to produce a dimming signal, evaluating electronics which control an electro-optical protective light filter, a controller to control the brightening time of the protective light filter, said controller detecting at least the intensity of the light impinging on the sensor; said controller being objectively connected to a timing generator to detect at least the duration of the dimming signal produced by the detector electronics; and said controller including means to interlink the acquired data with respect to logic and/or time.

2. Antiglare device as claimed in claim 1, wherein said control unit detects the course of the light intensity impinging on the sensor and produces a corresponding signal to control the brightening time of the protective light filter.

3. Antiglare device as claimed in claim 1, wherein said control unit produces a reset signal after each glare phase.

4. Antiglare device as claimed in claim 3, wherein the reset signal exhibits a delay relative to the end of the glare phase.

5. Antiglare device as claimed in claim 2, wherein said control unit detects the absolute value of the amount of light impinging on the sensor and a signal to control the brightening time of the protective light filter.

6. Antiglare device as claimed in claim 1, wherein said control unit generates a signal, which controls the slope of the dark/bright transition during the brightening time.

7. Antiglare device as claimed in claim 2, wherein said control unit generates a signal, which controls the slope of the dark/bright transition during the brightening time.

8. Antiglare device as claimed in claim 3, wherein said control unit generates a signal, which controls the slope of the dark/bright transition during the brightening time.

9. Antiglare device as claimed in claim 4, wherein said control unit generates a signal, which controls the slope of the dark/bright transition during the brightening time.

10. Antiglare device as claimed in claim 5, wherein said control unit generates a signal, which controls the slope of the dark/bright transition during the brightening time.

11. Antiglare device as claimed in claim 6, wherein the control unit generated signal is a function of an adjustable protective step.

12. Antiglare device as claimed in claim 7, wherein the control unit generated signal is a function of an adjustable protective step.

13. Antiglare device as claimed in claim 8, wherein the control unit generated signal is a function of an adjustable protective step.

14. Antiglare device as claimed in claim 9, wherein the control unit generated signal is a function of an adjustable protective step.

15. Antiglare device as claimed in claim 10, wherein the control unit generated signal is a function of an adjustable protective step.

* * * * *